United States Patent [19]

Kelly et al.

[11] Patent Number: 5,380,462
[45] Date of Patent: Jan. 10, 1995

[54] CYCLOHEXYL ALKENOATE COMPOUNDS

[75] Inventors: Stephen Kelly, Möhlin; Martin Schadt, Seltisberg, both of Switzerland

[73] Assignee: Hoffmann-La Roche Inc., Nutley, N.J.

[21] Appl. No.: 140,350

[22] Filed: Oct. 20, 1993

[30] Foreign Application Priority Data

Oct. 30, 1992 [CH] Switzerland .................. 3391/92

[51] Int. Cl.⁶ .............. C09K 19/30; C09K 19/34; C07C 69/533; C07D 213/28
[52] U.S. Cl. .............. 252/299.63; 252/299.61; 252/299.67; 544/298; 544/335; 546/339; 546/342; 549/369; 560/220
[58] Field of Search .............. 252/299.01, 299.61, 252/299.63, 299.66, 299.67; 560/220; 544/298, 335; 546/339, 342; 549/369; 359/103

[56] References Cited

U.S. PATENT DOCUMENTS

| | | | |
|---|---|---|---|
| 4,631,328 | 12/1986 | Ringsdorf et al. | 526/259 |
| 5,013,477 | 5/1991 | Buchecker et al. | 252/299.63 |
| 5,174,921 | 12/1992 | Buchecker et al. | 252/299.63 |
| 5,292,452 | 3/1994 | Buchecker et al. | 252/299.61 |

FOREIGN PATENT DOCUMENTS

| | | |
|---|---|---|
| 090282 | 3/1983 | European Pat. Off. . |
| 315050 | 10/1988 | European Pat. Off. . |
| 0351846 | 7/1989 | European Pat. Off. . |
| 458176 | 5/1991 | European Pat. Off. . |
| 475273 | 9/1991 | European Pat. Off. . |
| 546298 | 10/1992 | European Pat. Off. . |
| 91/15450 | 10/1991 | WIPO . |

OTHER PUBLICATIONS

Derwent Abstract No. 83-777855/40.
Derwent Abstract No. 89-139075/19.
Derwent Abstract No. 91-347898/48.
Derwent Abstract No. 92-089941/12.
Derwent Abstract No. 93-189731/24.
Derwent Abstract No. 91-304404/42.

Primary Examiner—Shean Wu
Attorney, Agent, or Firm—George M. Gould; George W. Johnston; John P. Parise

[57] ABSTRACT

Compounds having the Formula:

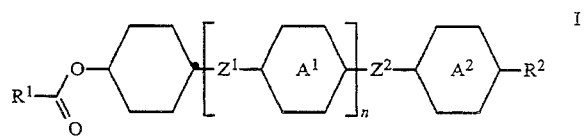

wherein $R^1$ denotes an alkenyl group;

$A^1$ and $A^2$ each independently represent 1,4-phenylene, which is unsubstituted or substituted with halogen and in which, when it is unsubstituted, optionally 1 or 2 CH group(s) is/are replaced by nitrogen, or trans-1,4-cyclohexylene or trans-1,3-dioxane-2,5-diyl;

$Z^1$ and $Z^2$ each independently signify a single covalent bond, $-CH_2CH_2-$, $-COO-$, $-OOC-$, $-OCH_2-$, $-CH_2O-$, $-C\equiv C-$, $-(CH_2)_4-$, $-O(CH_2)_3-$, $-(CH_2)_3O-$ or the trans form of $-OCH_2CH=CH-$, $-CH=CHCH_2O-$, $-(CH_2)_2CH=CH-$ or $-CH=CH(CH_2)_2-$;

n is either 0, 1 or 2; and $R^2$ is halogen, cyano or alkyl with 1 to 12 carbon atoms, which is optionally substituted with fluorine and in which optionally 1 $-CH_2-$ group or 2 non-adjacent $-CH_2-$ groups is/are replaced by oxygen, $-COO-$, $-OOC-$, $-CO-$ and/or a $-CH_2-CH_2-$ group is replaced by $-CH=CH-$, are useful in electro-optical applications. Liquid crystalline mixtures containing such compounds are especially suitable for use in commercial applications, such as electro-optic cells.

25 Claims, No Drawings

CYCLOHEXYL ALKENOATE COMPOUNDS

BACKGROUND OF THE INVENTION

1. Field

The present invention is concerned with novel compounds containing a cyclohexyl alkenoate residue, liquid crystalline mixtures containing such compounds, and the use of such compounds and mixtures for electro-optical purposes.

2. Description

Liquid crystals are used primarily as dielectrics in indicating devices, since the optical properties of such substances can be influenced by an applied voltage. Electro-optical devices based on liquid crystals are well-known and can employ various effects. Such devices are, for example, dynamic scattering cells, DAP cells ("deformation of aligned phases"), guest/host cells, TN cells ("twisted nematic" structure), STN cells ("super twisted nematic"), SBE cells ("super birefringence effect") and OMI cells ("optical mode interference"). Most common indicating devices are based on the Schadt-Helfrich effect and have a twisted nematic structure.

Liquid crystal materials should have good chemical and thermal stability as well as stability towards electric fields and electromagnetic radiation. At usual operating temperatures they should have a suitable mesophase, for example a nematic, cholesteric or tilted smectic phase. Moreover, liquid crystal materials should have low viscosity and, when used in cells, should give short response times, low threshold potentials and high contrast.

Other properties such as electrical conductivity, dielectric anisotropy and optical anisotropy must fulfill various requirements depending on the type of cell and field of application. For example, materials for cells having a twisted nematic structure should have positive dielectric anisotropy and minimal electrical conductivity. In addition to the general interest in liquid crystal materials having high optical anisotropy, there has recently been increased interest in materials exhibiting low optical anisotropy, especially for actively addressed liquid crystal displays, e.g. for TFT applications ("thin film transistor") in television sets.

Liquid crystals are typically used as mixtures of several components to optimize properties. It is therefore important that the components are readily miscibility.

Such compounds are provided by the present invention.

SUMMARY OF THE INVENTION

A compound is provided having the formula:

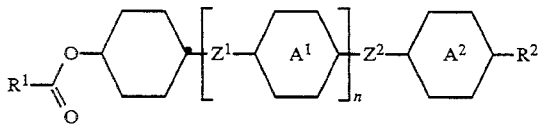

wherein $R^1$ is a $C_2$ to $C_{12}$ alkenyl;

$A^1$ and $A^2$ each independently is an unsubstituted 1,4-phenylene, halogen substituted 1,4-phenylene, unsubstituted 1,4-phenylene in which one of the CH groups is replaced by nitrogen, unsubstituted 1,4-phenylene in which two of the CH groups are replaced by nitrogen, trans-1,4-cyclohexylene, or trans-1,3-dioxane-2,5-diyl;

$Z^1$ and $Z^2$ each independently is a single covalent bond, $-CH_2CH_2-$, $-COO-$, $-OOC-$, $-OCH_2-$, $-CH_2O-$, $-C\!=\!C-$, $-(CH_2)_4-$, $-O(CH_2)_3-$, $-(CH_3)_3O-$, or the trans form of $-OCH_2CH\!=\!CH-$, $-CH\!=\!CHCH_2O-$, $-(CH_2)_2CH\!=\!CH-$ or $-CH\!=\!CH(CH_2)_2-$; n is 0, 1 or 2; and $R^2$ is halogen, cyano, $C_1$ to $C_{12}$ alkyl, $C_2$ to $C_{12}$ alkenyl, or $-Y^1-X-Y^2$ wherein X is COO, OOC, CO, O, or a covalent bond, and $Y^1$ and $Y^2$ each independently is $C_1$ to $C_{12}$ alkyl or $C_2$ to $C_{12}$ alkenyl, where the alkyl or alkenyl is unsubstituted or substituted with fluorine.

DETAILED DESCRIPTION OF THE INVENTION

The subject invention will now be described in terms of its preferred embodiments. These embodiments are set forth to aid in the understanding of the invention, but are not to be construed as limiting.

The compounds in accordance with the present invention have the formula:

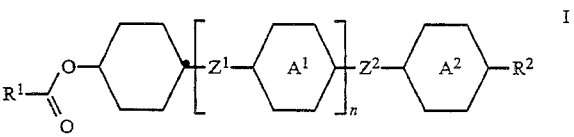

wherein $R^1$ denotes an alkenyl group;

$A^1$ and $A^2$ each independently represent 1,4-phenylene, which is unsubstituted or substituted with halogen and in which, when it is unsubstituted, optionally 1 or 2 CH group(s) is/are replaced by nitrogen, or trans-1,4-cyclohexylene or trans-1,3-dioxane-2,5-diyl;

$Z^1$ and $Z^2$ each independently signify a single covalent bond, $-CH_2CH_2-$, $-COO-$, $-OOC-$, $-OCH_2-$, $-CH_2O-$, $-C\!=\!C-$, $-(CH_2)_4-$, $-O(CH_2)_3-$, $-(CH_2)_3O-$ or the trans form of $-OCH_2CH\!=\!CH-$, $-CH\!=\!CHCH_2O-$, $-(CH_2)_2CH\!=\!CH-$ or $-CH\!=\!CH(CH_2)_2-$;

n is either 0, 1 or 2; and $R^2$ is halogen, cyano of alkyl with 1 to 12 carbon atoms, which is optionally substituted with fluorine and in which optionally 1 $-CH_2-$ group of 2 non-adjacent $-CH_2-$ groups is/are replaced by oxygen, $-COO-$, $-OOC-$, $-CO-$ and/or a $-CH_2-CH_2-$ group is replaced by $-CH\!=\!CH-$.

As used herein, the term "alkyl" embraces a straight or branched alkyl group with 1-12 carbon atoms ($C_1$ to $C_{12}$).

The term "alkoxy" is meant to describe the group $-OM$, wherein M is alkyl as defined above.

As used throughout the specification, the term "alkenyl" means a straight or branched chain alkyl group having at least one double bond.

The introduction of an alkenyl carboxyl group favorably influences the tendency to form liquid crystal phases, primarily the tendency to form a nematic phase. In nematic mixtures these esters produce high clearing points and surprisingly short switching times, thus often suppressing undesired smectic phases such as, for example, $S_B$ phases. The dielectric anisotropy ($\Delta\epsilon$) and the optical anisotropy ($\Delta n$) can be varied depending on the choice of rings and substituents. Thus, for example, compounds of formula I in which $R^2$ signifies cyano and $Z^2$ signifies —COO— have a high positive dielectric anisotropy. Compounds of formula I in which rings $A^1$ and $A^2$ represent 1,4-phenylene in which optionally one or two CH group(s) is/are replaced by nitrogen have, for example, a high optical anisotropy.

Preferred residues $R^1$ are alkenyl residues with 3 to 12 carbon atoms in which the double bond is present in the 1-position or in the 3-position and which have the E-configuration or alkenyl residues having a terminal double bond. Particularly preferred residues $R^1$ have 3 to 7 carbon atoms; such residues are, for example, 1E-propenyl, 1E-butenyl, 1E-pentenyl, 1E-hexenyl, 1E-heptenyl, 3-butenyl, 3E-pentenyl, 3E-hexenyl, 4-pentenyl, 5-hexenyl, 6-heptenyl and the like.

The term "1,4-phenylene, which is unsubstituted or substituted with halogen and in which optionally 1 or 2 CH group(s) is/are replaced by nitrogen," embraces in the scope of the present invention groups such as 1,4-phenylene, 2-fluoro-1,4-phenylene (i.e. in the ortho-position to the residue $R^2$), 2,3-difluoro-1,4-phenylene, 2,6-difluoro-1,4-phenylene, 2-chloro-1,4-phenylene, 2-bromo-1,4-phenylene, pyridine-2,5-diyl, pyrimidine-2,5-diyl and the like. Preferred groups are 1,4-phenylene, 2-fluoro-1,4-phenylene, 2,3-difluoro-1,4-phenylene, 2,6-difluoro-1,4-phenylene, pyridine-2,5-diyl, pyrimidine-2,5-diyl.

The term "halogen" denotes chlorine, fluorine, bromine and iodine, especially chlorine and fluorine.

The term "alkyl with 1 to 12 carbon atoms, which is optionally substituted with fluorine and in which optionally 1 —CH$_2$— group or 2 non-adjacent —CH$_2$— groups is/are replaced by oxygen, —CO—, —COO—, —OOC— and/or a —CH$_2$CH$_2$— group is replaced by —CH=CH—," denotes in the scope of the present invention straight-chain or branched (optionally chiral) residues such as alkyl, 1E-alkenyl, 3E-alkenyl, alkenyl having a terminal double bond, alkoxy, alkoxyalkyl, 2E-alkenyloxy, 3-alkenyloxy, alkenyloxy having a terminal double bond, alkenyloxyalkyl, haloalkyl, haloalkoxy, alkoxycarbonyl, alkanoyloxy and the like. Examples of preferred residues are methyl, ethyl, propyl, butyl, pentyl, hexyl, heptyl, octyl, nonyl, decyl, undecyl, dodecyl, vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 5-hexenyl, 6-heptenyl, 7-octenyl, 8-nonenyl, 9-decenyl, 10-undecenyl, 11-dodecenyl, methoxy, ethoxy, propyloxy, butyloxy, pentyloxy, hexyloxy, heptyloxy, octyloxy, nonyloxy, decyloxy, undecyloxy, dodecyloxy, allyloxy, 2E-butenyloxy, 2E-pentenyloxy, 2E-hexenyloxy, 2E-heptenyloxy, 3-butenyloxy, 3Z-pentenyloxy, 3Z-hexenyloxy, 3Z-heptenyloxy, 4-pentenyloxy, 5-hexenyloxy, 6-heptenyloxy, 7-octenyloxy, 8-nonenyloxy, 9-decenyloxy, 10-undecenyloxy, 11-dodecenyloxy, methoxymethyl, ethoxymethyl, propyloxymethyl, fluoromethyl, difluoromethyl, trifluoromethyl, fluoromethoxy, difluoromethoxy, trifluoromethoxy, trifluoroacetoxy and the like. Especially preferred residues $R^2$ have 1, or, respectively, 2 to 7 carbon atoms.

Preferred compounds of formula I are those in which n=0 or 1, especially those of formulae:

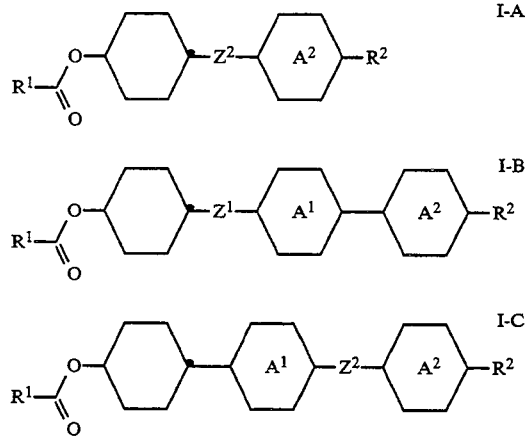

wherein
$R^1$ signifies alkenyl with 3 to 7 carbon atoms,
$A^1$ signifies 1,4-phenylene, which is unsubstituted or substituted with fluorine, or trans-1,4-cyclohexylene,
$A^2$ signifies 1,4-phenylene, which is unsubstituted or substituted with fluorine, pyrimidine-2,5-diyl, pyridine-2,5-diyl or trans-1,4-cyclohexylene,
$Z^1$, $Z^2$ each independently represent a single covalent bond, —CH$_2$CH$_2$—, —CH$_2$O—, —OCH$_2$—, —COO— or —OOC—, and
$R^2$ represents alkyl, alkoxy, alkenyl or alkenyloxy with 1 or, respectively, 2 to 7 carbon atoms or on aromatic ring also fluorine, chlorine or cyano.

The term "aromatic ring" embraces in the scope of the present invention 1,4-phenylene, which is unsubstituted or substituted with fluorine, pyrimidine-2,5-diyl or pyridine-2,5-diyl.

A preferred aspect of the invention is concerned with compounds of formulae I, I-A, I-B and I-C in which $R^1$ represents 1E-propenyl or 1E-butenyl and $R^2$ signifies alkyl or alkoxy with 1 to 7 carbon atoms. In the compounds of general formulae I, I-A, I-B and I-C preferably one of the groups $Z^1$ and $Z^2$ stands for a single covalent bond and the other of the groups $Z^1$ and $Z^2$ stands for a single covalent bond, —CH$_2$CH$_2$—, —COO— or —OOC—.

A particularly preferred aspect of this invention is concerned with the compounds of the formulae:

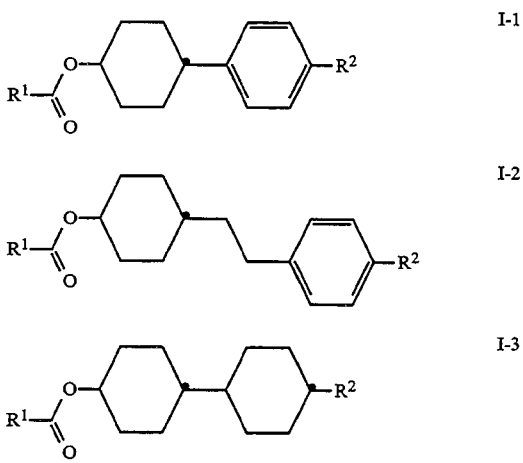

-continued

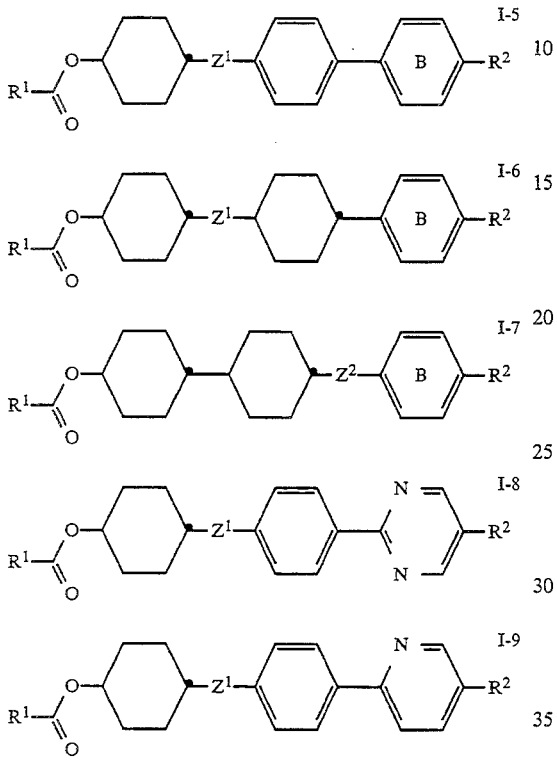

wherein
- R¹ represents 1E-propenyl or 1E-butenyl,
- Z¹, Z² signify a single covalent bond, —CH₂CH₂—, —COO— or —OOC—;
- ring B represents 1,4-phenylene, 2-fluoro-1,4-phenylene (i.e. in the ortho-position to the residue R²), 2,3-difluoro-1,4-phenylene, 2,6-difluoro-1,4-phenylene and
- R² signifies alkyl or alkoxy with 1 to 7 carbon atoms or on an aromatic ring also fluorine, chlorine or cyano.

In the compounds of formula I-A, especially in the compounds of formulae I-1 to I-4, R² preferably signifies alkyl or alkoxy with 1 to 5 carbon atoms. These compounds have a surprisingly broad nematic mesophase and a low viscosity.

The compounds of formulae I-B and I-C, especially those of formulae I-5 to I-9, in which R² signifies fluorine, chlorine or cyano and Z¹ or Z² signifies a single covalent bond or —CH₂CH₂— are, by virtue of their low threshold potential, particularly suitable for use in liquid crystal materials which are used for TFT cells.

Accordingly, the present invention provides a wide range of novel components for the further optimization and modification of liquid crystals materials.

The compounds of formula I can be prepared according to the method illustrated in the Scheme and in the Examples. The compounds of formula II are known compounds or analogues of known compounds; such compounds are described, for example, in U.S. Pat. Nos. 5,230,826 and 5,01 3,477, the contents of which are herein incorporated by reference.

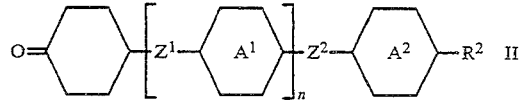

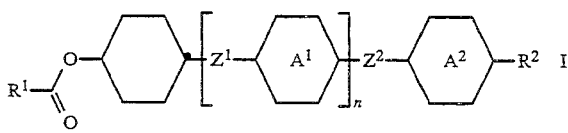

wherein R¹, R², Z¹, Z², A¹, A² and n have the significances defined in formula I.

The compounds of formula I can be used in the form of mixtures with one another and/or with other liquid crystal components.

The invention is therefore also concerned with liquid crystalline mixtures having at least two components, wherein at least one component is a compound of formula I. A second component and optionally additional components can be further compounds of general formula I or other suitable liquid crystal components. Suitable liquid crystal components will be known in large numbers by a person skilled in the art, e.g. from D. Demus et al., Flüsige Kristalle in Tabellen, VEB Deutscher Verlag für Grundstoffindustrie, Leipzig, volumes I and II, the content of which are herein incorporated by reference.

In view of the good solubility of the compounds of formula I in other liquid crystal materials and their good miscibility with one another, the content of compounds of formula I in the mixtures in accordance with the invention can be relatively high and can be, for example, 1–70 wt. %. In general, a content of about 3–40 wt. %, especially of about 5–30 wt. %, of compounds of formula 1 is preferred.

The mixtures in accordance with the invention preferably contain, in addition to one or more compounds of formula I, one or more compounds from the group of compounds of formulae:

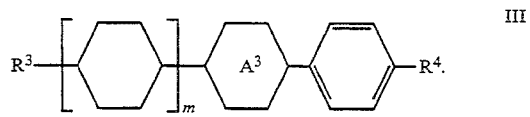

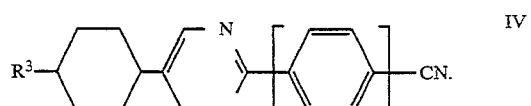

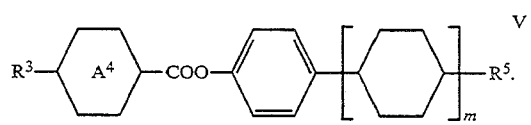

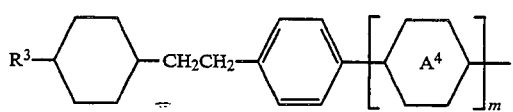 VI

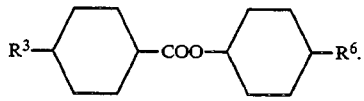 VII

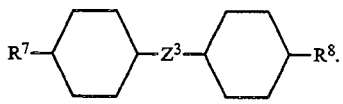 VIII

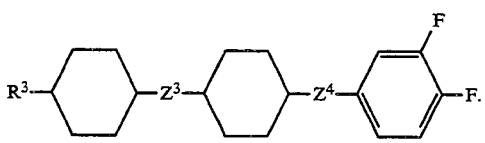 IX

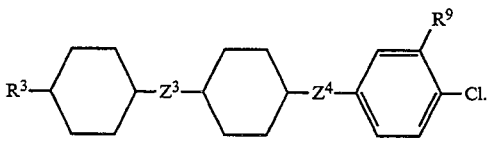 X

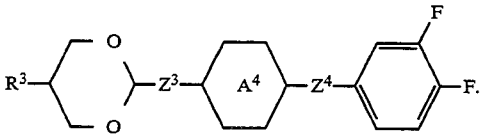 XI

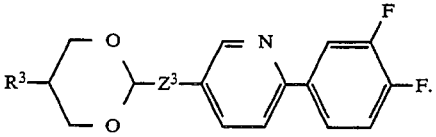 XII

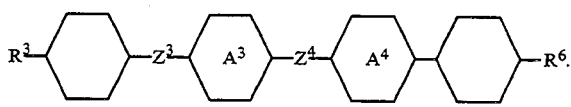 XIII

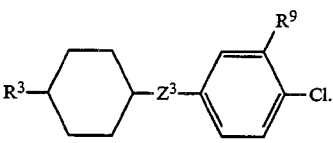 XIV

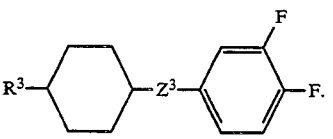 XV

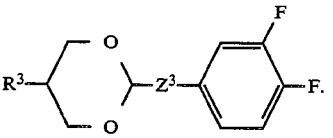 XVI

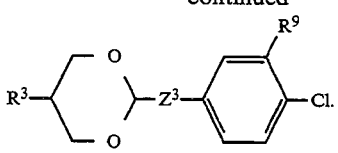 XVII

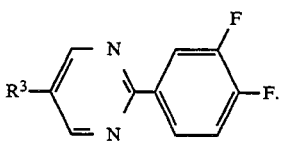 XVIII

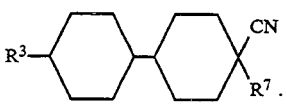 XIX

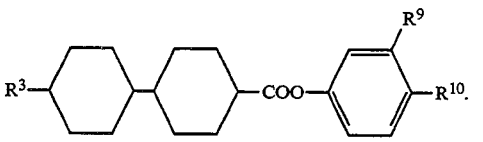 XX

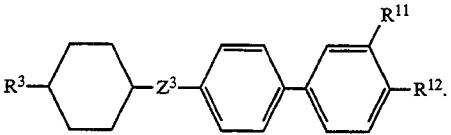 XXI wherein $R^3$, $R^6$ signify alkyl, alkoxyalkyl, 3E-alkenyl, 4-alkenyl or on saturated rings also 1E-alkenyl;

m signifies 0 or 1;

ring $A^3$ denotes 1,4-phenylene-2,5-diyl, pyridine-2,5-diyl, pyrimidine-2,5-diyl, trans-1,4-cyclohexylene or trans-1,3-dioxane-2,5-diyl;

$R^4$ represents cyano, isothiocyanato, fluorine, alkyl, 3E-alkenyl, 4-alkenyl, alkoxy, 2E-alkenyloxy, 3-alkenyloxy or 1-alkynyl;

ring $A^4$ signifies 1,4-phenylene or trans-1,4-cyclohexylene;

$R^5$ denotes alkyl, 3E-alkenyl, 4-alkenyl or on trans-1,4-cyclohexylene also 1 E-alkenyl or on 1,4-phenylene also cyano, isothiocyanato, alkoxy, 2E-alkenyloxy or 3-alkenyloxy;

$R^7$ signifies alkyl, 1E-alkenyl, 3E-alkenyl or 4-alkenyl;

$R^8$ represents cyano, alkyl, 1E-alkenyl, 3E-alkenyl, 4-alkenyl, alkoxy, 2E-alkenyloxy, 3-alkenyloxy, alkoxymethyl or (2E-alkenyl)oxymethyl;

$Z^3$, $Z^4$ denote a single covalent bond or —CH$_2$CH$_2$—, with two aromatic rings always being linked by a single covalent bond;

$R^9$ signifies hydrogen, fluorine or chlorine;

$R^{10}$ represents cyano, fluorine or chlorine;

$R^{11}$ denotes hydrogen or fluorine;

$R^{12}$ represents fluorine or chlorine.

The aforementioned term "aromatic rings" denotes in this connection rings such as, for example, 1,4-phenylene, pyridine-2,5-diyl or pyrimidine-2,5-diyl. The term "saturated rings" denotes trans-1,4-cyclohexylene or 1,3-dioxane-2,5-diyl.

Residues $R^3$ to $R^8$ each preferably have 1 or, respectively, 2 to 12 carbon atoms, especially 1 or, respectively, 2 to 7 carbon atoms. Straight-chain residues are generally preferred. The term "alkyl" preferably signifies in this connection straight-chain residues with 1 to 12 carbon atoms, preferably with 1 to 7 carbon atoms such as, for example, methyl, ethyl, propyl, butyl, pentyl, hexyl or heptyl.

The term "alkyoxyalkyl" preferably signifies in this connection straight-chain residues such as, for example, methoxymethyl, ethoxymethyl, propyloxymethyl, butyloxymethyl and the like.

The term "alkyloxy" preferably signifies in this connection straight-chain residues such as, for example, methoxy, ethoxy, propyloxy, butyloxy, pentyloxy, hexyloxy, heptyloxy and the like.

The term "1E-alkenyl" preferably signifies in this connection straight-chain alkenyl residues in which the double bond is situated in the 1-position, such as, for example, vinyl, 1E-propenyl, 1E-butenyl, 1E-pentenyl, 1E-hexenyl, 1E-heptenyl and the like.

The term "3E-alkenyl" preferably signifies in this connection straight-chain alkenyl residues in which the double bond is situated in the 3-position, such as, for example, 3-butenyl, 3E-pentenyl, 3E-hexenyl, 3E-heptenyl and the like.

The term "4-alkenyl" preferably signifies in this connection straight-chain alkenyl residues in which the double bond is situated in the 4-position, such as, for example, 4-pentenyl, 4-hexenyl, 4-heptenyl and the like.

The term "2E- or 3-alkenyloxy" preferably signifies in this connection straight-chain alkenyloxy residues in which the double bond is situated in the 2- or 3-position and E or Z indicates the preferred configuration, such as, for example, allyloxy, 2E-butenyloxy, 2E-pentenyloxy, 2E-hexenyloxy, 2E-heptenyloxy, 3-butenyloxy, 3-pentenyloxy, 3-hexenyloxy, 3-heptenyloxy, 4-pentenyloxy, 5-hexenyloxy, 6-heptenyloxy and the like.

The term "1-alkynyl" preferably signifies in this connection straight-chain alkynyl residues in which the triple bond is situated in the 1-position, such as, for example, ethynyl, 1-propynyl, 1-butynyl, 1-pentynyl and the like.

The mixtures in accordance with the invention can also contain optically active compounds (e.g. optically active 4'-alkyl- or 4'-alkoxy-4-biphenylcarbonitriles) and/or dichroic colouring substances (e.g. azo, azoxy or anthraquinone colouring substances). The content of such compounds is determined by the solubility, the desired pitch, colour, extension and the like. In general, the content of optically active compounds and dichroic colouring substances is in each case a maximum of about 10 wt. % in the final mixture.

The manufacture of the mixtures in accordance with the invention and the manufacture of the electro-optical devices can be effected by these skilled in the art who have read this disclosure.

The preparation of the compounds of formula I and of liquid crystalline mixtures containing these compounds are illustrated in more detail by the following Examples. C signifies a crystalline phase, F signifies a smectic phase, N signifies a nematic phase and I signifies the isotropic phase. V10 denotes the voltage for 10% transmission (viewing angle perpendicular to the plate surface). $t_{on}$ and $t_{off}$ denote, respectively, the switching-on time and the switching-off time and an denotes the optical anisotropy.

Unless indicated otherwise, the Examples were carried out as written. All compounds listing melting points, or other data, have actually been prepared.

EXAMPLE 1

4.2 g of N,N'-dicyclohexylcarbodiimide are added at 0° C. within 5 minutes while stirring to a solution of 5.0 g of trans-4-(trans-4-[3,4difluorophenyl]cyclohexyl)-cyctohexan-1-ol, 1.5 g of crotonic acid and 0.05 g of 4-(dimethylamino)pyridine in 50 ml of dichloromethane. The reaction mixture is stirred at room temperature overnight, then filtered, the filtrate is washed with saturated sodium bicarbonate solution and with water and concentrated. Chromatographic purification of the residue on silica gel with hexane/ethyl acetate (vol. 9:1 ) and two-fold recrystallization of the fractions which are pure according to thin-layer chromatography gives 2.0 g of trans-4-(trans-4-[3,4-difluorophenyl]cyclohexyl)cyclohexyl (E)-2-butenoate. m.p. (C-N) 103° C. and cl.p. (N-I) 201° C.

The trans-4-(trans-4-[3,4-difluorophenyl]cyclohexyl)-cyclohexan1-ol used as the starting material is prepared as follows:

A mixture of 32 g of sodium borohydride and 180 ml of ethanol are treated with 165 ml of water at 0° C., stirred for 10 minutes, then treated dropwise at 0°-5° C. with a solution of 50 g of trans-4-(trans-4-[3,4-difluorophenyl]cyclohexyl)cyclohexanone in 1 00 ml of ethanol and 10 ml of dichloromethane. The reaction mixture is stirred at 0° C. for a further 30 minutes, then poured into 1 00 ml of dichloromethane and washed twice with 100 ml of water each time. The combined aqueous phases are extracted twice with 50 ml of dichloromethane each time. The combined organic phases are then washed twice with 100 ml of water each time, dried over magnesium sulphate, the suspension is filtered and the filtrate is concentrated. The residue is recrystallized from tert. butyl methyl ether. This gives 35 g of trans-4-(trans-4-[3,4-difluorophenyl]cyclohexyl) cyclohexan-1-ol, m.p. (C-I) 144°-145° C.

The following compounds can be prepared in an analogous manner:

trans-4-(trans-4-[3,4-difluorophenyl]cyclohexyl)cyclohexyl 3-butenoate.
trans-4-(trans-4-[3,4-difluorophenyl]cyclohexyl)cyclohexyl (E)-2-pentenoate.
trans-4-(trans-4-[3,4-difluorophenyl]cyclohexyl)cyclohexyl 4-pentenoate.
trans-4-(trans-4-[4-fluorophenyl]cyclohexyl)cyclohexyl (E)-2-butenoate, m.p. (C-N) 105° C., cl.p. (N-I) 219° C.
trans-4-(trans-4-[4-fluorophenyl]cyclohexyl)cyclohexyl 3-butenoate.
trans-4-(trans-4-[4-fluorophenyl]cyclohexyl)cyclohexyl (E)-2-pentenoate.
trans-4-(trans-4-[4-fluorophenyl]cyclohexyl)cyclohexyl pentenoate.
trans-4-(trans-4-[4-chlorophenyl]cyclohexyl)cyclohexyl (E)-2-butenoate, m.p. (C-N) I 29° C., cl.p. (N-I) 257° C.
trans-4-(trans-4-[4-chlorophenyl]cyclohexyl)cyclohexyl 3-butenoate.
trans-4-(trans-4-[4-chlorophenyl]cyclohexyl)cyclohexyl (E)-2-pentenoate.
trans-4-(trans-4-[4-chlorophenyl]cyclohexyl)cyclohexyl 4-pentenoate.
trans-4-(trans-4-[4-chloro-3-fluorophenyl]cyclohexyl)cyclohexyl (E)-2-butenoate, top. (C-N) 134° C., mp. (N-I) 233° C.
trans-4-(trans-4-[4-chloro-3-fluorophenyl]cyclohexyl)cyclohexyl 3-butenoate.

trans-4-(trans-4-[4-chloro-3-fluorophenyl]cyclohexyl)cyclohexyl (E)-2-pentenoate.
trans-4-(trans-4-[4-chloro-3-fluorophenyl]cyclohexyl)cyclohexyl 4-pentenoate.
trans-4-(trans-4-[4-bromophenyl]cyclohexyl)cyclohexyl (E)-2-butenoate.
trans-4-(trans-4-[4-bromophenyl]cyclohexyl)cyclohexyl 3-butenoate.
trans-4-(trans-4-[4-bromophenyl]cyclohexyl)cyclohexyl (E)-2-pentenoate.
trans-4-(trans-4-[4-bromophenyl]cyclohexyl)cyclohexyl 4-pentenoate.
trans-4-(trans-4-[4-bromo-3-fluorophenyl]cyclohexyl)cyclohexyl (E)-2-butenoate.
trans-4-(trans-4-[4-bromo-3-fluorophenyl]cyclohexyl)cyclohexyl 3-butenoate.
trans-4-(trans-4-[4-bromo-3 -fluorophenyl]cyclohexyl)cyclohexyl (E)-2-pentenoate.
trans-4-(trans-4-[4-bromo-3-fluorophenyl]cyclohexyl)cyclohexyl 4-pentenoate.
trans-4-(trans-4-[4-cyanophenyl]cyclohexyl)cyclohexyl (E)-2-butenoate.
trans-4-(trans-4-[4-cyanophenyl]cyclohexyl)cyclohexyl 3-butenoate.
trans-4-(trans-4-[4-cyanophenyl]cyclohexyl)cyclohexyl (E)-2-pentenoate.
trans-4-(trans-4-[4-cyanophenyl]cyclohexyl)cyclohexyl 4-pentenoate.
trans-4-(trans-4-[4-cyano-3-fluorophenyl]cyclohexyl)cyclohexyl (E)-2-butenoate.
trans-4-(trans-4-[4-cyano-3-fluorophenyl]cyclohexyl)cyclohexyl 3-butenoate.
trans-4-(trans-4-[4-cyano-3-fluorophenyl]cyclohexyl)cyclohexyl (E)-2-pentenoate.
trans-4-(trans-4-[4-cyano-3-fluorophenyl]cyclohexyl)cyclohexyl 4-pentenoate.
trans-4-(trans-4-[4-trifluoromethoxyphenyl]cyclohexyl)cyclohexyl (E)-2-butenoate, m.p. (C-N) 83° C., cl.p. (N-I) 229° C.
trans-4-(trans-4-[4-trifluoromethoxyphenyl]cyclohexyl)cyclohexyl 3-butenoate.
trans-4-(trans-4-[4-trifluoromethoxyphenyl]cyclohexyl)cyclohexyl (E)-2-pentenoate.
trans-4-(trans-4-[4-trifluoromethoxyphenyl]cyclohexyl)cyclohexyl 4-pentenoate.
trans-4-(trans-4-[4-difluoromethoxyphenyl]cyclohexyl)cyclohexyl (E)-2-butenoate.
trans-4-(trans-4-[4-difluoromethoxyphenyl]cyclohexyl)cyclohexyl 3-butenoate.
trans-4-(trans-4-[4-difluoromethoxyphenyl]cyclohexyl)cyclohexyl (E)-2-pentenoate.
trans-4-(trans-4-[4-difluoromethoxyphenyl]cyclohexyl)cyclohexyl 4-pentenoate, m.p. (C-N) 157° C., cl.p. (N-I) 199° C.
trans-4-(trans-4-[4-trifluoromethylphenyl]cyclohexyl)cyclohexyl (E)-2-butenoate.
trans-4-(trans-4-[4-trifluoromethylphenyl]cyclohexyl)cyclohexyl 3-butenoate.
trans-4-(trans-4-[4-trifluoromethylphenyl]cyclohexyl)cyclohexyl (E)-2-pentenoate.
trans-4-(trans-4-[4-trifluoromethylphenyl]cyclohexyl)cyclohexyl 4-pentenoate.
trans-4-(trans-4-[4-trifluoroacetophenyl]cyclohexyl)cyclohexyl (E)-2-butenoate.
trans-4-(trans-4-[4-trifluoroacetophenyl]cyclohexyl)cyclohexyl 3 -butenoate.
trans-4-(trans-4-[4-trifluoroacetophenyl]cyclohexyl)cyclohexyl (E)- 2-pentenoate.
trans-4-(trans-4-[4-trifluoroacetophenyl]cyclohexyl)cyclohexyl 4-pentenoate.
trans-4-(trans-4-[4-methylphenyl]cyclohexyl)cyclohexyl (E)-2-butenoate.
trans-4-(trans-4-[4-methylphenyl]cyclohexyl)cyclohexyl 3-butenoate.
trans-4-(trans-4-[4-methylphenyl]cyclohexyl)cyclohexyl (E)-2-pentenoate.
trans-4-(trans-4-[4-methylphenyl]cyclohexyl)cyclohexyl 4-pentenoate.
trans-4-(trans-4-[4-ethylphenyl]cyclohexyl)cyclohexyl (E)-2-butenoate.
trans-4-(trans-4-[4-ethylphenyl]cyclohexyl)cyclohexyl 3-butenoate.
trans-4-(trans-4-[4-ethylphenyl]cyclohexyl)cyclohexyl (E)-2-pentenoate.
trans-4-(trans-4-[4-ethylphenyl]cyclohexyl) cyclohexyl 4-pentenoate.
trans-4-(trans-4-[4-propylphenyl]cyclohexyl)cyclohexyl (E)-2-butenoate.
trans-4-(trans-4-[4-propylphenyl]cyclohexyl)cyclohexyl 3-butenoate.
trans-4-(trans-4-[4-propylphenyl]cyclohexyl)cyclohexyl (E)-2-pentenoate.
trans-4-(trans-4-[4-propylphenyl]cyclohexyl)cyclohexyl 4-pentenoate.
trans-4-(trans-4-[4-methoxyphenyl]cyclohexyl)cyclohexyl (E)-2-butenoate.
trans-4-(trans-4-[4-methoxyphenyl]cyclohexyl)cyclohexyl 3-butenoate.
trans-4-(trans-4-[4-methoxyphenyl]cyclohexyl)cyclohexyl (E)-2-pentenoate.
trans-4-(trans-4-[4-methoxyphenyl]cyclohexyl)cyclohexyl 4-pentenoate.
trans-4-(trans-4-[4-ethoxyphenyl]cyclohexyl)cyclohexyl (E)-2-butenoate.
trans-4-(trans-4-[4-ethoxyphenyl]cyclohexyl)cyclohexyl 3-butenoate.
trans-4-(trans-4-[4-ethoxyphenyl]cyclohexyl)cyclohexyl (E)-2-pentenoate.
trans-4-(trans-4-[4-ethoxyphenyl]cyclohexyl)cyclohexyl 4-pentenoate.
trans-4-(trans-4-[2-(4-fluorophenyl)ethyl]cyclohexyl)cyclohexyl (E)-2-butenoate.
trans-4-(trans-4-[2-(4-chlorophenyl)ethyl]cyclohexyl)cyclohexyl (E)-2-butenoate.
trans-4-(trans-4-[2-( 4-bromophenyl)ethyl]cyclohexyl)cyclohexyl (E)-2-butenoate.
trans-4-(trans-4-[2-( 4-cyanophenyl)ethyl]cyclohexyl)cyclohexyl (E)-2-butenoate.
trans-4-(trans-4-[Z-(3,4-difluorophenyl)ethyl]cyclohexyl)-cyclohexyl (E)-2-butenoate.
trans-4-(trans-4-[2-(4-chloro-3-fluorophenyl)ethyl]cyclohexyl)cyclohexyl (E)-2-butenoate.
trans-4-[2-(trans-4-[2-( 4-fluorophenyl)ethyl]cyclohexyl)ethyl]cyclohexyl 3-butenoate.
trans-4-[2-(trans-4-[2-(4-chlorophenyl)ethyl]cyclohexyl)ethyl]cyclohexyl 3-butenoate.
trans-4-[2-(trans-4-[2-(4-bromophenyl)ethyl]cyclohexyl)ethyl]cyclohexyl 3-butenoate.
trans-4-[2-(trans-4-[2-(4-cyanophenyl)ethyl]cyclohexyl)ethyl]cyclohexyl 3-butenoate.
trans-4-[2-(trans-4-[2-(3,4-difluorophenyl)ethyl]cyclohexyl)ethyl]cyclohexyl 3-butenoate.
trans-4-[2-(trans-4-[2-(4-chloro-3-fluorophenyl)ethyl]cyclohexyl)ethyl]cyclohexyl)ethyl]cyclohexyl 3-butenoate.

trans-4-[3,4-difluorophenyl]cyclohexyl (E)-2-butenoate.
trans-4-[3,4-difluorophenyl]cyclohexyl 3-butenoate.
trans-4-[3,4-difluorophenyl]cyclohexyl (E)-2-pentenoate.
trans-4-[3,4-difluorophenyl]cyclohexyl 4-pentenoate.
trans-4-[4-fluorophenyl]cyclohexyl (E)-2-butenoate.
trans-4-[4-fluorophenyl]cyclohexyl 3-butenoate.
trans-4-[4-fluorophenyl]cyclohexyl (E)-2-pentenoate.
trans-4-[4-fluorophenyl]cyclohexyl 4-pentenoate.
trans-4-[4-chlorophenyl]cyclohexyl (E)-2-butenoate.
trans-4-[4-chlorophenyl]cyclohexyl 3-butenoate.
trans-4-[4-chlorophenyl]cyclohexyl (E)-2-pentenoate.
trans-4-[4-chlorophenyl]cyclohexyl 4-pentenoate.
trans-4-[4-chloro-3-fluorophenyl]cyclohexyl (E)-2-butenoate.
trans-4-[4-chloro-3-fluorophenyl]cyclohexyl 3-butenoate.
trans-4-[4-chloro-3-fluorophenyl]cyclohexyl (E)-2-pentenoate.
trans-4-[4-chloro-3-fluorophenyl]cyclohexyl 4-pentenoate.
trans-4-[4-bromophenyl]cyclohexyl (E)-2-butenoate.
trans-4-[4-bromophenyl]cyclohexyl 3-butenoate.
trans-4-[4-bromophenyl]cyclohexyl (E)-2-pentenoate.
trans-4-[4-bromophenyl]cyclohexyl 4-pentenoate.
trans-4-[4-bromo-3-fluorophenyl]cyclohexyl (E)-2-butenoate.
trans-4-[4-bromo-3-fluorophenyl]cyclohexyl 3-butenoate.
trans-4-[4-bromo-3-fluorophenyl]cyclohexyl (E)-2-pentenoate.
trans-4-[4-bromo-3-fluorophenyl]cyclohexyl 4-pentenoate.
trans-4-[4-cyanophenyl]cyclohexyl (E)-2-butenoate, m.p. (C-I) 128° C., cl.p. (N-I) 119° C.
trans-4-[4-cyanophenyl]cyclohexyl 3-butenoate.
trans-4-[4-cyanophenyl]cyclohexyl (E)-2-pentenoate.
trans-4-[4-cyanophenyl]cyclohexyl 4-pentenoate.
trans-4-[4-cyano-3-fluorophenyl]cyclohexyl (E)-2-butenoate.
trans-4-[4-cyano-3-fluorophenyl]cyclohexyl 3-butenoate.
trans-4-[4-cyano-3-fluorophenyl]cyclohexyl (E)-2-pentenoate.
trans-4-[4-cyano-3-fluorophenyl]cyclohexyl 4-pentenoate.
trans-4-[4-trifluoromethoxyphenyl]cyclohexyl (E)-2-butenoate.
trans-4-[4-trifluoromethoxyphenyl]cyclohexyl 3-butenoate.
trans-4-[4-trifluoromethoxyphenyl]cyclohexyl (E)-2-pentenoate.
trans-4-[4-trifluoromethoxyphenyl]cyclohexyl)cyclohexyl 4-pentenoate.
trans-4-[4-difluoromethoxyphenyl]cyclohexyl 3-butenoate.
trans-4-[4-difluoromethoxyphenyl]cyclohexyl (E)-2-pentenoate.
trans-4-[4-difluoromethoxyphenyl]cyclohexyl 4-pentenoate.
trans-4-[4-trifluoromethylphenyl]cyclohexyl (E)-2-butenoate.
trans-4-[4-trifluoromethylphenyl]cyclohexyl 3-butenoate.
trans-4-[4-trifluoromethylphenyl]cyclohexyl (E)-2-pentenoate.
trans-4-[4-trifluoromethylphenyl]cyclohexyl 4-pentenoate.
trans-4-[4-trifluoroacetophenyl]cyclohexyl (E)-2-butenoate.
trans-4-[4-trifluoroacetophenyl]cyclohexyl 3-butenoate.
trans-4-[4-trifluoroacetophenyl]cyclohexyl (E)-2-pentenoate.
trans-4-[4-trifluoroacetophenyl]cyclohexyl 4-pentenoate.
trans-4-[4-methylphenyl]cyclohexyl (E)-2-butenoate.
trans-4-[4-methylphenyl]cyclohexyl 3-butenoate.
trans-4-[4-methylphenyl]cyclohexyl (E)-2-pentenoate.
trans-4-[4-methylphenyl]cyclohexyl 4-pentenoate.
trans-4-[4-ethylphenyl]cyclohexyl (E)-2-butenoate.
trans-4-[4-ethylphenyl]cyclohexyl 3-butenoate.
trans-4-[4-ethylphenyl]cyclohexyl (E)-2-pentenoate.
trans-4-[4-ethylphenyl]cyclohexyl 4-pentenoate.
trans-4-[4-propylphenyl]cyclohexyl (E)-2-butenoate, m.p. (C-I) 71° C., cl.p. (N-I) 47° C.
trans-4-[4-propylphenyl]cyclohexyl 3-butenoate.
trans-4-4-[4-propylphenyl]cyclohexyl (E)-2-pentenoate.
trans-4-[4-propylphenyl]cyclohexyl 4-pentenoate.
trans-4-[4-methoxyphenyl]cyclohexyl (E)-2-butenoate, m.p. (C-N) 74° C., cl.p. (N-I) 89° C.
trans-4-[4-methoxyphenyl]cyclohexyl 3-butenoate.
trans-4-[4-methoxyphenyl]cyclohexyl (E)-2-pentenoate.
trans-4-[4-methoxyphenyl]cyclohexyl 4-pentenoate.
trans-4-[4-ethoxyphenyl]cyclohexyl (E)-2-butenoate, m.p. (C-N) 78° C., cl.p. (N-I) 110° C.
trans-4-[4-ethoxyphenyl]cyclohexyl-(E) 2-pentenoate, m.p. (C-I) 84° C., cl.p. (n-i) 80° C.
trans-4-[4-ethoxyphenyl]cyclohexyl-(E) 2-hexenoate, m.p. (C-N) 53° C., cl.p. (n-I) 86° C.
trans-4-[4-ethoxyphenyl]cyclohexyl-(E) 2-heptenoate, m.p. (C-N) 46° C., cl.p. (N-I) 68° C.
trans-4-[4-ethoxyphenyl]cyclohexyl-(E) 2-octenoate, m.p. (C-N) 55° C., cl.p. (N-I) 72° C.
trans-4-[4-propyloxyphenyl]cyclohexyl (E)-2-butenoate, m.p. (C-N) 65° C., cl.p. (N-I) 87° C.
trans-4-[4-butoxyphenyl]cyclohexyl (E)-2-butenoate, m.p. (C-N) 59° C., cl.p. (N-I) 92° C.
trans-4-[4-pentyloxyphenyl]cyclohexyl (E)-2-butenoate, top. (C-N) 75° C., cl.p. (N-I) 79° C.
trans-4-[4-hexyloxyphenyl]cyclohexyl (E)-2-butenoate, top. (C-N) 67° C., cl.p. (N-I) 80° C.
trans-4-[4-heptyloxyphenyl]cyclohexyl (E)-2-butenoate,mp. (C-N) 61° C., cl.p. (N-I) 74° C.
trans-4-[2-(4-fluorophenyl)ethyl]cyclohexyl (E)-2-butenoate, m.p. (C-I) 62° C.
trans-4-[2-(4-chlorophenyl)ethyl]cyclohexyl (E)-2-butenoate, m.p. (C-I) 73° C., cl.p. (N-I) 45° C.
trans-4-[2-(4-bromophenyl)ethyl]cyclohexyl (E)-2-butenoate.
trans-4-[2-(4-trifluoromethoxyphenyl)ethyl]cyclohexyl (E)-2butenoate.
trans-4-[2-(4-trifluoromethylphenyl)ethyl]cyclohexyl (E)-2-butenoate.
trans-4-[2-(4-cyanophenyl)ethyl]cyclohexyl (E)-2-butenoate.
trans-4-[2-(3,4-difluorophenyl)ethyl]cyclohexyl (E)-2-butenoate.

trans-4-[2-(4-chloro-3-fluorophenyl)ethyl]cyclohexyl (E)-2-butenoate.

trans-4-(4-[3,4-difluoro-4'-biphenyl])cyclohexyl (E)-2-butenoate, m.p. (C-N) 113° C., cl.p. (N-I) 184° C.

trans-4-(4-[3,4-difluoro-4'-biphenyl])cyclohexyl 3-butenoate.

trans-4-(4-[3,4-difluoro-4'-biphenyl])cyclohexyl (E)-2-pentenoate.

trans-4-(4-[3,4-difluoro-4'-biphenyl])cyclohexyl 4-pentenoate.

trans-4-(4-[4-fluoro-4'-biphenyl])cyclohexyl (E)-2-butenoate, m.p. (Co N) 122° C., cl.p. (N-I) 216° C.

trans-4-(4-[4-fluoro-4'-biphenyl])cyclohexyl 3-butenoate.

trans-4-(4-[4-fluoro-4'-biphenyl])cyclohexyl (E)-2-pentenoate.

trans-4-(4-[4-fluoro-4'-biphenyl])cyclohexyl 4-pentenoate.

trans-4-(4-[4-chloro-4'-biphenyl])cyclohexyl (E)-2-butenoate.

trans-4-(4-[4-chloro-4'-biphenyl])cyclohexyl 3-butenoate.

trans-4-(4-[4-chloro-4'-biphenyl])cyclohexyl (E)-2-pentenoate.

trans-4-(4-[4-chloro-4'-biphenyl])cyclohexyl 4-pentenoate.

trans-4-(t4-[4-chloro-3-fluoro-4'-biphenyl])cyclohexyl (E)-2-butenoate.

trans-4-(4-[4-chloro-3-fluoro-4'-biphenyl])cyclohexyl 3-butenoate.

trans-4-(4-[4-chloro-3-fluoro-4'-biphenyl])cyclohexyl (E)-2-pentenoate.

trans-4-(4-[4-chloro-3-fluoro-4'-biphenyl])cyclohexyl 4-pentenoate.

trans-4-(4-[4-bromo-4'-biphenyl])cyclohexyl (E)-2-butenoate.

trans-4-(4-[4-bromo-4'-biphenyl])cyclohexyl 3-butenoate.

trans-4-(4-[4-bromo-4'-biphenyl])cyclohexyl (E)-2-pentenoate.

trans-4-(4-[4-bromo-4'-biphenyl])cyclohexyl 4-pentenoate.

trans-4-(4-[4-bromo-3-fluoro-4'-biphenyl])cyclohexyl (E)-2-butenoate.

trans-4-(4-[4-bromo-3-fluoro-4'-biphenyl])cyclohexyl 3-butenoate.

trans-4-(4-[4-bromo-3-fluoro-4'-biphenyl])cyclohexyl (E)-2-pentenoate.

trans-4-(4-[4-bromo-3-fluoro-4'-biphenyl])cyclohexyl 4-pentenoate.

trans-4-(4-[4-cyano-4'-biphenyl])cyclohexyl (E)-2-butenoate, m.p. (C-N) 171° C., cl.p. (N-I) ~290° C.

trans-4-(4-[4-cyano-4'-biphenyl])cyclohexyl 3-butenoate.

trans-4-(4-[4-cyano-4'-biphenyl])cyclohexyl (E)-2-pentenoate.

trans-4-(4-[4-cyano-4'-biphenyl])cyclohexyl 4-pentenoate.

trans-4-(4-[4-cyano-3-fluoro-4'-biphenyl])cyclohexyl (E)-2-butenoate.

trans-4-(4-[4-cyano-3-fluoro-4'-biphenyl])cyclohexyl 3-butenoate.

trans-4-(4-[4-cyano-3-fluoro-4'-biphenyl])cyclohexyl (E)-2-pentenoate.

trans-4-(4-[4-cyano-3-fluoro4'-biphenyl])cyclohexyl 4-pentenoate.

trans-4-(4-[4-trifluoromethoxy-4'-biphenyl])cyclohexyl (E)-2-butenoate.

trans-4-(4-[4-trifluoromethoxy-4'-biphenyl])cyclohexyl 3-butenoate.

trans-4-(4-[4-trifluoromethoxy-4'-biphenyl])cyclohexyl (E)-2-pentenoate.

trans-4-(4-[4-trifluoromethoxy-4'-biphenyl])cyclohexyl 4-pentenoate.

trans-4-(4-[4-difluoromethoxy-4'-biphenyl])cyclohexyl (E)-2-butenoate.

trans-4-(4-[4-difluoromethoxy-4'-biphenyl])cyclohexyl 3-butenoate.

trans-4-(4-[4-difluoromethoxy-4'-biphenyl])cyclohexyl (E)-2pentenoate.

trans-4-(4-[4-difluoromethoxy-4'-biphenyl])cyclohexyl 4-pentenoate.

trans-4-(4-[4-trifluoromethyl-4'-biphenyl])cyclohexyl (E)-2-butenoate.

trans-4-(4-[4-trifluoromethyl-4'-biphenyl])cyclohexyl 3-butenoate.

trans-4-(4-[4-trifluoromethyl-4'-biphenyl])cyclohexyl (E)-2-pentenoate.

trans-4-(4-[4-trifluoromethyl-4'-biphenyl])cyclohexyl 4-pentenoate.

trans-4-(trans-4-[4-trifluoroaceto-4'-biphenyl])cyclohexyl (E)-2butenoate.

trans-4-(trans-4-[4-trifluoroaceto-4'-biphenyl])cyclohexyl 3 -butenoate.

trans-4-(trans-4-[4-trifluoroaceto-4'-biphenyl])cyclohexyl (E)-2-pentenoate.

trans-4-(trans-4-[4-trifluoroaceto-4'-biphenyl])cyclohexyl 4-pentenoate.

trans-4-(4-[4-ethyl-4'-biphenyl)cyclohexyl (E)-2-butenoate.

trans-4-(4-[4-ethyl-4'-biphenyl)cyclohexyl 3-butenoate.

trans-4-(4-[4-ethyl-4'-biphenyl)cyclohexyl (E)-2-pentenoate.

trans-4-(4-[4-ethyl-4'-biphenyl)cyclohexyl 4-pentenoate.

trans-4-(4-[4-propyl-4'-biphenyl)cyclohexyl (E)-2-butenoate.

trans-4-(4-[4-propyl-4'-biphenyl)cyclohexyl 3-butenoate.

trans-4-(4-[4-propyl-4'-biphenyl)cyclohexyl (E)-2-pentenoate.

trans-4-(4-[4-propyl-4'-biphenyl)cyclohexyl 4-pentenoate.

trans-4-(4-[4-methoxy-4'-biphenyl)cyclohexyl (E)-2-butenoate.

trans-4-(4-[4-methoxy-4'-biphenyl)cyclohexyl 3-butenoate.

trans-4-(4-[4-methoxy-4'-biphenyl)cyclohexyl (E)-2-pentenoate.

trans-4-(4-[4-methoxy-4'-biphenyl)cyclohexyl 4-pentenoate.

trans-4-(4-[4-ethoxy-4'-biphenylcyclohexyl (E)-2-butenoate.

trans-4-(4-[4-ethoxy-4'-biphenyl)cyclohexyl 3-butenoate.

trans-4-(4-[4-ethoxy-4'-biphenyl)cyclohexyl (E)-2-pentenoate.

trans-4-(4-[4-ethoxy-4'-biphenyl)cyclohexyl 4-pentenoate.

trans-4-(4-[2,3-difluoro-4-methoxy-4'-biphenyl)cyclohexyl (E)-2-butenoate, m.p. (C-N) 155° C., cl.p. (N-I) 234° C.

trans-4-(4-[2,3-difluoro-4-ethoxy-4'-biphenyl)cyclohexyl (E)-2-butenoate, m.p. (C-N) 120° C., cl.p. (N-I) 240° C.

trans-4-(4-[2,3-difluoro-4-propoxy-4'-biphenyl)cyclohexyl (E)-2-butenoate, m.p. (C-N) 96° C., cl.p. (N-I) 225° C.

trans-4-(4-[2,3-difluoro-4-butoxy-4'-biphenyl)cyclohexyl (E)-2-butenoate, m.p. (C-N) 103° C., cl.p. (N-I) 218°-C.

trans-4-(4-[2,3-difluoro-4-pentyloxy-4'-biphenyl)cyclohexyl (E)-2-butenoate, m.p. (C-N) 105° C., cl.p. (N-I) ;201° C.

trans-4-(4-[2,3-difluoro-4-hexyloxy-4'-biphenyl)cyclohexyl (E)-2-butenoate, m.p. (C-N) 76° C., cl.p. (N-I) 195° C.

trans-4-(4-[2,3-difluoro-4-heptyloxy-4'-biphenyl)cyclohexyl (E)-2-butenoate, m.p. (C-N) 74° C., cl.p. (N-I) 186° C.

trans-4-(4-[2,3-difluoro-4-octyloxy-4'-biphenyl)cyclohexyl (E)-2-butenoate, m.p. (C-N) 67° C., cl.p. (N-I) 181° C.

trans-4-(4-[2,3-difluoro-4-nonyloxy-4'-biphenyl)cyclohexyl (E)-2-butenoate, m.p. (C-N) 81° C., cl.p. (N-I) 174° C.

trans-4-(4-[2,3-difluoro-4-decyloxy-4'-biphenyl)cyclohexyl (E)-2-butenoate, m.p. (C-N) 71° C., cl.p. (N-I) 170° C.

trans-4-(4-[2,3-difluoro-4-undecyloxy-4'-biphenyl)cyclohexyl (E)-2-butenoate, m.p. (C-N) 81° C., cl.p. (N-I) 164° C.

trans-4-(4-[2,3-difluoro-4-dodecyloxy-4'-biphenyl)cyclohexyl (E)-2-butenoate.

trans-4-(trans-4-cyanocyclohexyl)cyclohexyl (E)-2-butenoate.

trans-4-(trans-4-methylcyclohexyl)cyclohexyl (E)-2-butenoate.

trans-4-(trans-4-methylcyclohexyl)cyclohexyl 3-butenoate.

trans-4-(trans-4-methylcyclohexyl)cyclohexyl (E)-2-pentenoate.

trans-4-(trans-4-methylcyclohexyl)cyclohexyl 4-pentenoate.

trans-4-(trans-4-ethylcyclohexyl)cyclohexyl (E)-2-butenoate.

trans-4-(trans-4-ethylcyclohexyl)cyclohexyl 3-butenoate.

trans-4-(trans-4-ethylcyclohexyl)cyclohexyl (E)-2-pentenoate.

trans-4-(trans-4-ethylcyclohexyl)cyclohexyl 4-pentenoate.

trans-4-(trans-4-propylcyclohexyl)cyclohexyl (E)-2-butenoate, m.p. (C-N) 77° C., cl.p. (N-I) 172° C.

trans-4-(trans-4-propylcyclohexyl)cyclohexyl 3-butenoate.

trans-4-(trans-4-propylcyclohexyl)cyclohexyl (E)-2-pentenoate.

trans-4-(trans-4-propylcyclohexyl)cyclohexyl 4-pentenoate.

trans-4-(trans-4-butylcyclohexyl)cyclohexyl (E)-2-butenoate, m.p. (C-N) 67° C., cl.p. (N-I) 122° C.

trans-4-(trans-4-butylcyclohexyl)cyclohexyl 3-butenoate.

trans-4-(trans-4-butylcyclohexyl)cyclohexyl (E)-2-pentenoate.

trans-4-(trans-4-butylcyclohexyl)cyclohexyl 4-pentenoate.

trans-4-(trans-4-pentylcyclohexyl)cyclohexyl (E)-2-butenoate, m.p. (C-N) 74° C., cl.p. (N-I) 131° C.

trans-4-(trans-4-pentylcyclohexyl)cyclohexyl 3-butenoate.

trans-4-(trans-4-pentylcyclohexyl)cyclohexyl (E)-2-pentenoate.

trans-4-(trans-4-pentylcyclohexyl)cyclohexyl 4-pentenoate.

trans-4-[2-(trans-4-methylcyclohexyl)ethyl]cyclohexyl (E)-2-butenoate.

trans-4-[2-(trans-4-methylcyclohexyl)ethyl]cyclohexyl 3-butenoate.

trans-4-[2-(trans-4-methylcyclohexyl)ethyl]cyclohexyl (E)-2-pentenoate.

trans- b 4-[2-(trans-4-methylcyclohexyl)ethyl]cyclohexyl 4-pentenoate.

trans-4-[2-(trans-4-ethylcyclohexyl)ethyl]cyclohexyl (E)-2-butenoate.

trans-4-[2-(trans-4-ethylcyclohexyl)ethyl]cyclohexyl 3-butenoate.

trans-4-[2-(trans-4-ethylcyclohexyl)ethyl]cyclohexyl (E)-2-pentenoate.

trans-4-[2-(trans-4-ethylcyclohexyl)ethyl]cyclohexyl 4-pentenoate.

trans-4-[2-(trans-4-propylcyclohexyl)ethyl]cyclohexyl (E)-2butenoate, m.p. (C-N) 44° C., cl.p. (N-I) 109° C.

trans-4-[2-(trans-4-propylcyclohexyl)ethyl]cyclohexyl 3-butenoate.

trans-4-[2-(trans-4-Propylcyclohexyl)ethyl]cyclohexyl (E)-2-pentenoate, m.p. (C-S$_B$) 46° C. S$_B$-N, 62° C., cl.p. (N-I) 86° C.

trans-4-[2-(trans-4-propylcyclohexyl)ethyl]cyclohexyl 4-pentenoate.

trans-4-[2-(trans-4-propylcyclohexyl)ethyl]cyclohexyl (E)-2-hexenoate, m.p. (C-S$_B$) 43° C., S$_B$-N, 69° C., cl.p. (N-I) 89° C.

trans-4-[2-(trans-4-propylcyclohexyl)ethyl]cyclohexyl (E)-2-heptenoate, m.p. (C-S$_B$) 25° C. S$_B$-N, 71° C., cl.p. (N-I) 78° C.

trans-4-[2-(trans-4-propylcyclohexyl)ethyl]cyclohexyl (E)-2-octenoate, m.p. (C-S$_B$) 39° C., S$_B$-N, 72° C., cl.p. (N-I) 83° C.

trans-4-[4-(5-pentyl-2-pyrimidinyl)phenyl]cyclohexyl (E)-2-butenoate trans-4-[4-(5-pentyl-2-pyrimidinyl)phenyl]cyclohexyl (E)-2-pentenoate.

trans-4-[4-(5-pentyl-2-pyrimidinyl)phenyl]cyclohexyl (E)-2-hexenoate.

trans-4-[4-(5-pentyl-2-pyrimidinyl)phenyl]cyclohexyl (E)-2-heptenoate.

trans-4-[4-(5-pentyl-2-pyrimidinyl)phenyl]cyclohexyl (E)-2-octenoate.

trans-4-[4-(5-pentyl-2-pyrimidinyl)phenyl]cyclohexyl (E)-2-nonenoate.

trans-4-[4-(5-pentyl-2-pyrimidinyl)phenyl]cyclohexyl (E)-2-decenoate.

trans-4-[4-(5-pentyl-2-pyrimidinyl)phenyl]cyclohexyl (E)-2-undecenoate.

trans-4-[4-(5-pentyl-2-pyrimidinyl)phenyl]cyclohexyl (E)-2-dodecenoate.

trans-4-[4-(5-pentyl-2-pyridinyl)phenyl]cyclohexyl (E)-2-butenoate.

trans-4-[4-(5-pentyl-2-pyridinyl)phenyl]cyclohexyl (E)-2-pentenoate.

trans-4-[4-(5-pentyl-2-pyridinyl)phenyl]cyclohexyl (E)-2-hexenoate.

trans-4-[4-(5-pentyl-2-pyridinyl)phenyl]cyclohexyl (E)-2-heptenoate.

trans-4-[4-(5-pentyl-2-pyridinyl)phenyl]cyclohexyl (E)-2-octenoate.

trans-4-[4-(5-pentyl-2-pyridinyl)phenyl]cyclohexyl (E)-2-nonenoate.

trans-4-[4-(5-pentyl-2-pyridinyl)phenyl]cyclohexyl (E)-2-decenoate.

trans-4-[4-(5-pentyl-2-pyridinyl)phenyl]cyclohexyl (E)-2-undecenoate.

trans-4-[4-(5-pentyl-2-pyridinyl)phenyl]cyclohexyl (E)-2-dodecenoate.

EXAMPLE 2

0.7 g of 4-pentylphenol, 1.0 g of trans-4-[(E)-2-butenoyloxy)cyclohexanecarboxylic acid and 0.05 g of 4-(dimethylamino)pyridine in ml of dichloromethane are converted into 4-pentylphenyl trans-4-[(E)-2-butenoyloxy)cyclohexanoate in an analogous manner to Example 1.

The trans-4-[(E)-2-butenoyloxy)cyclohexanecarboxylic acid used as the starting material is prepared as follows:

A solution of crotonoyl chloride in 20 ml of dichloromethane is added dropwise at 0° C. while stirring within 15 minutes to a solution of 8.7 g of 4-trans-hydroxycyclohexanecarboxylic acid, 10 ml of triethylamine and 100 ml of dichloromethane. The reaction mixture is stirred at 0° C. for 20 minutes and then at room temperature overnight, poured into water and extracted three times with 50 ml of ethyl acetate each time. The combined organic phases are washed twice with ml of water each time, dried over magnesium sulphate, filtered and subsequently concentrated. Recrystallization from hexane gives 6.3 g of trans-4-[(E)-2-butenoyloxy)cyclohexanecarboxylic acid.

The following compounds can be prepared in an analogous manner:

4-Methylphenyl trans-4-[(E)-2-butenoyloxy]cyclohexanoate.

4-ethylphenyl trans-4-[(E)-2-butenoyloxy]cyclohexanoate.

4-propylphenyl trans-4-[(E)-2-butenoyloxy]cyclohexanoate.

4-butylphenyl trans-4-[(E)-2-butenoyloxy]cyclohexanoate.

4-hexylphenyl trans-4-[(E)-2-butenoyloxy]cyclohexanoate.

4-heptylphenyl trans-4-[(E)-2-butenoyloxy]cyclohexanoate.

4-methoxyphenyl trans-4-[(E)-2-butenoyloxy]cyclohexanoate.

4-ethoxyphenyl trans-4-[(E)-2-butenoyloxy]cyclohexanoate.

4-propyloxyphenyl trans-4-[(E)-2-butenoyloxy]cyclohexanoate.

4-butyloxyphenyl trans-4-[(E)-2-butenoyloxy]cyclohexanoate.

4-pentyloxyphenyl trans-4-[(E)-2-butenoyloxy]cyclohexanoate.

4-hexyloxyphenyl trans-4-[(E)-2-butenoyloxy]cyclohexanoate.

4-fluorophenyl trans-4-[(E)-2-butenoyloxy]cyclohexanoate.

4-chlorophenyl trans-4-[(E)-2-butenoyloxy]cyclohexanoate.

4-cyanophenyl trans-4-[(E)-2-butenoyloxy]cyclohexanoate.

4-trifluoromethylphenyl trans-4-[(E)-2-butenoyloxy]cyclohexanoate.

4-trifluoromethoxyphenyl trans-4-[(E)-2-butenoyloxy]cyclohexanoate.

3,4-difluorophenyl trans-4-[(E)-2-butenoyloxy]cyclohexanoate.

3-fluoro-4-chlorophenyl trans-4-[(E)-2-butenoyloxy]cyclohexanoate.

3-fluoro-4-cyanophenyl trans-4-[(E)-2-butenoyloxy]cyclohexanoate.

4-methylphenyl trans-4-(trans-4-[(E)-2-butenoyloxy]cyclohexyl)cyclohexanoate.

4-ethylphenyl trans-4-(trans-4-[(E)-2-butenoyloxy]cyclohexyl)cyclohexanoate.

4-propylphenyl trans-4-(trans-4-[(E)-2-butenoyloxy]cyclohexyl)cyclohexanoate.

4-butylphenyl trans-4-(trans-4-[(E)-2-butenoyloxy]cyclohexyl)cyclohexanoate.

4-pentylphenyl trans-4-(trans-4-[(E)-2-butenoyloxy]cyclohexyl)cyclohexanoate.

4-hexylphenyl trans-4-(trans-4-[(E)-2-butenoyloxy]cyclohexyl)cyclohexanoate.

4-methoxyphenyl trans-4-(trans-4-[(E)-2-butenoyloxy]cyclohexyl)cyclohexanoate.

4-ethoxyphenyl trans-4-(trans-4-[(E)-2-butenoyloxy]cyclohexyl)cyclohexanoate.

4-propyloxyphenyl trans-4-(trans-4-[(E)-2-butenoyloxy]cyclohexyl)cyclohexanoate.

4-butyloxyphenyl trans-4-(trans-4-[(E)-2-butenoyloxy]cyclohexyl)cyclohexanoate.

4-pentyloxyphenyl trans-4-(trans-4-[(E)-2-butenoyloxy]cyclohexyl)cyclohexanoate.

4-hexyloxyphenyl trans-4-(trans-4-[(E)-2-butenoyloxy]cyclohexyl)cyclohexanoate.

4-fluorophenyl trans-4-(trans-4-[(E)-2-butenoyloxy]cyclohexyl)cyclohexanoate.

4-chlorophenyl trans-4-(trans-4-[(E)-2-butenoyloxy]cyclohexyl)cyclohexanoate.

4-cyanophenyl trans-4-(trans-4-[(E)-2-butenoyloxy]cyclohexyl)cyclohexanoate.

4-trifluoromethylphenyl trans-4-(trans-4-[(E)-2-butenoyloxy]cyclohexyl)cyclohexanoate.

4-trifluoromethoxyphenyl trans-4-(trans-4-[(E)-2-butenoyloxy]cyclohexyl)cyclohexanoate.

3,4-difluorophenyl trans-4-(trans-4-[(E)-2-butenoyloxy]cyclohexyl)cyclohexanoate.

3-fluoro-4-chlorophenyl trans-4-(trans-4-[(E)-2-butenoyloxy]cyclohexyl)cyclohexanoate.

3-fluoro-4-cyanophenyl trans-4-(trans-4-[(E)-2-butenoyloxy]cyclohexyl)cyclohexanoate.

4-trans-methylcyclohexyl trans-4-[(E)-2-butenoyloxy]cyclohexanoate.

4-trans-ethylcyclohexyl trans-4-[(E)-2-butenoyloxy]cyclohexanoate.

4-trans-propylcyclohexyl trans-4-[(E)-2-butenoyloxy]cyclohexanoate.

4-trans-butylcyclohexyl trans-4-[(E)-2-butenoyloxy]cyclohexanoate.

4-trans-pentylcyclohexyl trans-4-[(E)-2-butenoyloxy]cyclohexanoate.

4-trans-hexylcyclohexyl trans-4-[(E)-2-butenoyloxy]cyclohexanoate.

4-trans-heptylcyclohexyl trans-4-[(E)-2-butenoyloxy]cyclohexanoate.

4-trans-cyanocyclohexyl trans-4-[(E)-2-butenoyloxy]cyclohexanoate.

4-trans-methylcyclohexyl trans-4-(trans-4-[(E)-2-butenoyloxy]cyclohexyl)cyclohexanoate.

4-trans-ethylcyclohexyl trans-4-(trans-4-[(E)-2-butenoyloxy]cyclohexyl)cyclohexanoate.

4-trans-propylcyclohexyl trans-4-(trans-4-[(E)-2-butenoyloxy]cyclohexyl)cyclohexanoate.

4-trans-butylcyclohexyl trans-4-(trans-4-[(E)-2-butenoyloxy]cyclohexyl)cyclohexanoate.
4-trans-pentylcyclohexyl trans-4-(trans-4-[(E)-2-butenoyloxy]cyclohexyl)cyclohexanoate.
4-trans-hexylcyclohexyl trans-4-(trans-4-[(E)-2-butenoyloxy]cyclohexyl)cyclohexanoate.
4-trans-heptylcyclohexyl trans-4-(trans-4- [(E)-2-butenoyloxy]cyclohexyl)cyclohexanoate.
4-trans-cyanocyclohexyl trans-4-(trans-4-[(E)-2-butenoyloxy]cyclohexyl)cyclohexanoate.

EXAMPLE 3

Binary mixtures (BM) with 4-(trans-4-pentylcyclohexyl)benzonitrile were prepared in order to investigate the properties of the compounds of formula I in mixtures. The threshold potentials were measured at 22° C. in a TN cell (low bias tilt) having a plate separation of 8 μm; the 2.5-fold value of the threshold potential ($V_{10}$) was chosen as the operating voltage. The clearing point (cl.p. (N-I), the threshold potential ($V_{10}$), the switching-on time ($t_{on}$), the switching-off time ($t_{off}$) and the optical anisotropy (Δn) were measured. The corresponding data for 4-(trans-4-pentylcyclohexyl)benzonitrile are: cl.p. (N-I) 54.6° C., $V_{10}$=1.62V, ton=22 ms, $t_{off}$=40 ms and Δn =0.120.

BM-1

90 wt. % of 4-(trans-4-pentylcyclohexyl)benzonitrile
10 wt. % of trans-4-(trans-4-[3,4-difluorophenyl]cyclohexyl)cyclohexyl (E)-2-butenoate;
cl.p. (N-I)=61.8 ° C., $V_{10}$=1.66 V, $t_{on}$=27 ms, $t_{off}$=44 ms, Δn=0.123.

BM-2

80 wt. % of 4-(trans-4-pentylcyclohexyl)benzonitrile
20 wt. % of trans-4-(trans-4-[3,4-difluorophenyl]cyclohexyl)cyclohexyl (E)-2-butenoate;
cl.p. (N-I)=70.2 ° C., $V_{10}$=1.70 V, $t_{on}$=32 ms, $t_{off}$=52 ms, Δn=0.124.

The subject invention has been described in terms of its preferred embodiments. Upon reading the specification, various alternative embodiments will become obvious to those skilled in the art. These embodiments are to be considered within the scope and spirit of the invention, which is only to be limited by the claims which follow and their equivalents.

What is claimed is:

1. A compound of the formula:

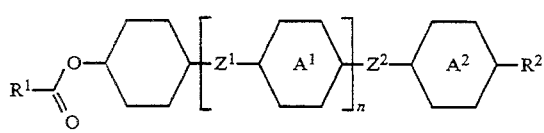

wherein
$R^1$ is a $C_2$ to $C_{12}$ alkenyl;
$A^1$ and $A^2$ each independently is an unsubstituted 1,4-phenylene, halogen substituted 1,4-phenylene, unsubstituted 1,4-phenylene in which one of the CH groups is replaced by nitrogen, unsubstituted 1,4-phenylene in which two of the CH groups are replaced by nitrogen, trans-1,4-cyclohexylene, or trans-1, 3-dioxane-2,5-diyl;
$Z^1$ and $Z^2$ each independently is a single covalent bond, —CH$_2$CH$_2$—, —COO—, —OOC—, —OCH$_2$—, —CH$_2$O—, —C≡C—, —(CH$_2$)$_4$—, —O (CH$_2$)$_3$—, —(CH$_2$)$_3$O—, or the trans form of —OCH$_2$CH=CH—, —CH=CHCH$_2$O—, —(CH$_2$)$_2$CH=CH— or —CH=CH (CH$_2$)$_2$—; n is 0, 1 or 2; and
$R^2$ is halogen, cyano, $C_1$ to $C_{12}$ alkyl, $C_2$ to $C_{12}$ alkenyl, or
—y$^1$—X—Y$^2$
wherein
X is COO, OOC, CO, O, or a covalent bond,
y$^1$ is either not present or present as $C_1$ to $C_{12}$ alkyl or $C_2$ to $C_{12}$ alkenyl, where the alkyl or alkenyl is unsubstituted or substituted with at least one fluorine, and
y$^2$ is $C_1$ to $C_{12}$ alkyl $C_2$ to $C_{12}$ alkenyl, where the alkyl or alkenyl is unsubstituted or substituted with at least one fluorine.

2. The compound of claim 1, wherein n is 0 or 1.

3. The compound of claim 1, wherein $R^1$ is 1 E-propenyl, 1E-butenyl, 1E-pentenyl, 1E-hexenyl, 1E-heptenyl, 3-butenyl, 3E-pentenyl, 3E-hexenyl, 4-pentenyl, 5-hexenyl, or 6-heptenyl.

4. The compound of claim 1, wherein $A^1$ and $A^2$ each independently is 1,4-phenylene, 2-fluoro-1,4-phenylene, 2,3-difluoro-1,4-phenylene, 2,6-difluoro-1,4-phenylene, 2-chloro-1,4-phenylene, 2-bromo-1,4-phenylene, pyridine-2,5-diyl, or pyrimidine-2,5-diyl.

5. The compound of claim 1, wherein $R^2$ is methyl, ethyl, propyl, butyl, pentyl, hexyl, heptyl, octyl, nonyl, decyl, undecyl, dodecyl, vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 5-hexenyl, 6-heptenyl, 7-octenyl, 8-nonenyl, 9-decenyl, 10-undecenyl, 11-dodecenyl, methoxy, ethoxy, propyloxy, butyloxy, pentyloxy, hexyloxy, heptyloxy, octyloxy, nonyloxy, decyloxy, undecyloxy, dodecyloxy, allyloxy, 2E-butenyloxy, 2E-pentenyloxy, 2E-hexenyloxy, 2E-heptenyloxy, 3-butenyloxy, 3Z-pentenyloxy, 3Z-hexenyloxy, 3Z-heptenyloxy, 4-pentenyloxy, 5-hexenyloxy, 6-heptenyloxy, 7-octenyloxy, 8-nonenyloxy, 9-decenyloxy, 10-undecenyloxy, 11-dodecenyloxy, methoxymethyl, ethoxymethyl, propyloxymethyl, fluoromethyl, difluoromethyl, trifluoromethyl, fluoromethoxy, difluoromethoxy, trifluoromethoxy, or trifluoroacetoxy.

6. The compound of claim 1 having the formula:

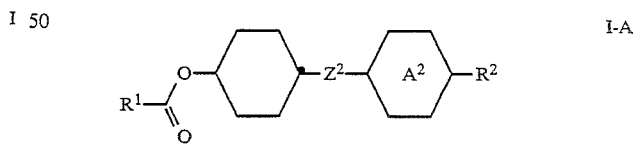

wherein
$R^1$ is an unsubstituted alkenyl group having 3 to 7 carbon atoms;
$A^2$ is unsubstituted 3,4-phenylene, fluorine substituted 1,4-phenylene, pyrimidine-2,5 -diyl, pyridine-2,5-diyl or trans-1,4-cyclohexylene;
$Z^2$ is a single covalent bond, —CH$_2$CH$_2$—, —CH$_2$O—, —OCH$_2$—, —COO— or —OOC—; and
$R^2$ is an unsubstituted alkyl, alkoxy, alkenyl or alkenyloxy of 7 or less carbon atoms, or when $A^2$ is an aromatic ring, also fluorine, chlorine or cyano.

7. The compound of claim 1 having the formula:

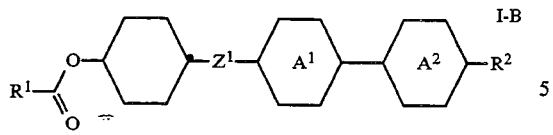
I-B wherein
R¹ is an unsubstituted alkenyl of 3 to 7 carbon atoms;
A¹ is unsubstituted 1,4-phenylene, fluorine substituted 1,4-phenylene, or trans-1,4-cyclohexylene;
A² is unsubstituted 1,4-phenylene, fluorine substituted 1,4-phenylene, pyrimidine-2,5-diyl, pyridine-2,5-diyl or trans-1,4-cyclohexylene;
Z¹ is a single covalent bona, —CH₂CH₂—, —CH₂O—, —OCH₂—, —COO— or —OOC—, and
R² is an unsubstituted alkyl, alkoxy, alkenyl or alkenyloxy of 7 or less carbon atoms, or when A² is an aromatic ring, also fluorine, chlorine or cyano.

8. The compound of claim 1 having the formula:

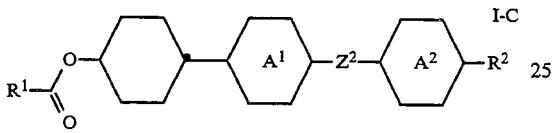
I-C wherein
R¹ is an unsubstituted alkenyl of 3 to 7 carbon atoms;
A¹ is unsubstituted 1,4-phenylene, fluorine substituted 1,4-phenylene, or trans-1,4-cyclohexylene;
A² is unsubstituted 1,4-phenylene, fluorine substituted 1,4-phenylene, pyrimidine-2,5-diyl, pyridine-2,5-diyl or trans-1,4-cyclohexylene;
Z² is a single covalent bond, —CH₂CH₂—, —CH₂O—, —OCH₂—, —COO— or —OOC—, and
R² is an unsubstituted alkyl, alkoxy, alkenyl or alkenyloxy of 7 or less carbon atoms, or when A² is an aromatic ring, also fluorine, chlorine or cyano.

9. A compound of claim 1, wherein one of Z¹ and Z² is a single covalent bond and the other of Z1 and Z² is a single covalent bond, —CH₂CH₂—, —COO— or —OOC—.

10. The compound of claim 1 having the formula:

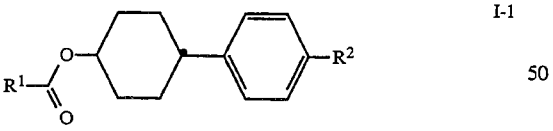
I-1 wherein R¹ is 1E-propenyl or 1E-butenyl; and R² is alkyl or alkoxy of 1 to 7 carbon atoms, fluorine, chlorine or cyano.

11. The compound of claim 1 having the formula:

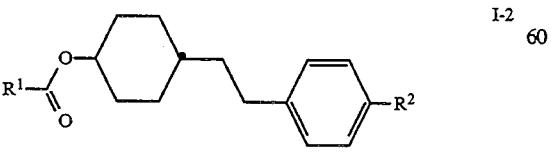
I-2 wherein R1 is 1E-propenyl or 1E-butenyl; and R2 is alkyl or alkoxy of from 1 to 7 carbon atoms, fluorine, chlorine or cyano.

12. The compound of claim 1 having the formula:

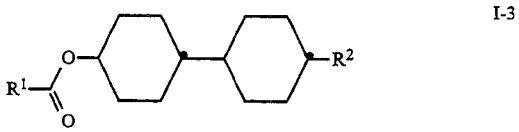
I-3 wherein R¹ is 1E-propenyl or 1E-butenyl; and R² is alkyl or alkoxy of from 1 to 7 carbon atoms.

13. The compound of claim I having the formula:

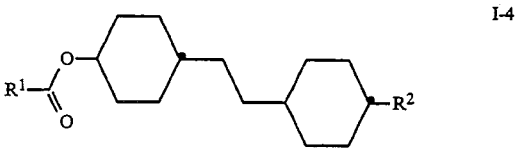
I-4 wherein R1 is 1E-propenyl or 1E-butenyl; and R² is alkyl or alkoxy of from 1 to 7 carbon atoms.

14. The compound of claim 1 having the formula:

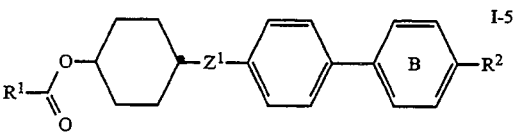
I-5 wherein
R¹ is 1E-propenyl or 1E-butenyl;
Z¹ is a single covalent bond, —CH₂CH₂—, —COO— or —OOC—;
B is 1,4-phenylene, 2-fluoro-1,4-phenylene, 2,3-difluoro-1,4-phenylene, 2,6-difluoro-1,4-phenylene; and
R² is alkyl or alkoxy of from 1 to 7 carbon atoms, fluorine, chlorine or cyano.

15. The compound of claim 1 having the formula:

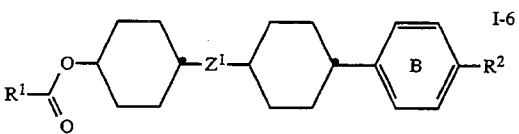
I-6 wherein
R¹ is 1E-propenyl or 1E-butenyl;
Z¹ is a single covalent bond, —CH₂CH₂—, —COO— or —OOC—;
B is 1,4-phenylene, 2-fluoro-1,4-phenylene (ortho to residue R²), 2,3-difluoro-1,4-phenylene, 2,6-difluoro-1,4-phenylene; and
R² is alkyl or alkoxy of from 1 to 7 carbon atoms, fluorine, chlorine or cyano.

16. The compound of claim 1 having the formula:

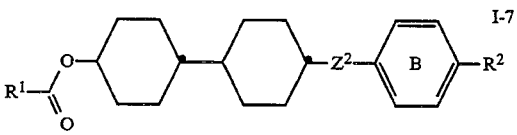
I-7 wherein
R¹ is 1E-propenyl or 1E-butenyl;

$Z^2$ is a single covalent bond, —CH$_2$CH$_2$—, —COO— or —OOC—;

B is 1,4-phenylene, 2-fluoro-1,4-phenylene (ortho to residue R$^2$), 2,3-difluoro-1,4-phenylene, 2,6-difluoro-1,4-phenylene; and R$^2$ is alkyl or alkoxy of from 1 to 7 carbon atoms, fluorine, chlorine or cyano.

17. A compound having the formula:

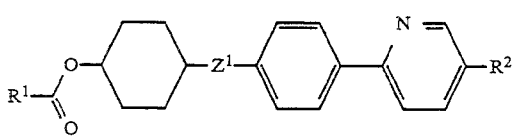

wherein

R$^1$ is 1E-propenyl or 1E-butenyl;

Z$^1$ is a single covalent bond, —CH$_2$CH$_2$—, —COO— or —OOC—; and

R$^2$ is alkyl or alkoxy of from 1 to 7 carbon atoms, fluorine, chlorine or cyano.

18. A compound having the formula:

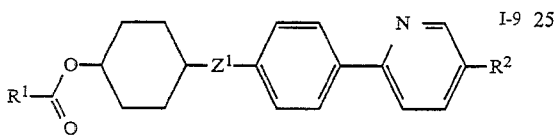

I-9 wherein

R$^1$ is 1E-propenyl or 1E-butenyl;

Z$^1$ is a single covalent bond, —CH$_2$CH$_2$—, —COO— or —OOC—; and

R$^2$ is alkyl or alkoxy of from 1 to 7 carbon atoms, fluorine, chlorine or cyano.

19. The compound of claim 14, wherein Z$^1$ is a single covalent bond or —CH$_2$CH$_2$—.

20. The compound of claim 15, wherein Z$^1$ is a single covalent bond or —CH$_2$CH$_2$—.

21. The compound of claim 16, wherein Z$^2$ is a single covalent bond or —CH$_2$CH$_2$—.

22. The compound of claim 17, wherein Z$^1$ is a single covalent bond or —CH$_2$CH$_2$—.

23. The compound of claim 18, wherein Z$^1$ is a single covalent bond or —CH$_2$CH$_2$—.

24. A liquid crystalline; composition having at least two components, one of such components comprising a compound having the formula:

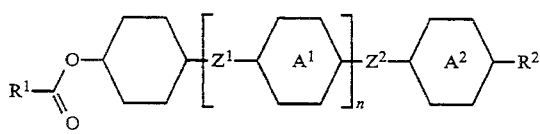

wherein

R$^1$ is a C$_2$ to C$_{12}$ alkenyl;

A$^1$ and A$^2$ each independently is an unsubstituted 1,4-phenylene, halogen substituted 1,4-phenylene, unsubstituted 1,4-phenylene in which one of the CH groups is replaced by nitrogen, unsubstituted 1,4-phenylene in which two of the CH groups are replaced by nitrogen, trans-1,4-cyclohexylene, or trans-1,3-dioxane-2,5-diyl;

Z$^1$ and Z$^2$ each independently is a single covalent bond, —CH$_2$CH$_2$—, —COO—, —OOC—, —OCH$_2$—, —CH$_2$O—, —C≡C—, —(CH$_2$)$_4$—, —O(CH$_2$)$_3$—, —(CH$_2$)$_3$C—, or the trans form of —OCH$_2$CH═CH—, —CH═CHCH$_2$O—, —(CH$_2$)$_2$CH═CH— or —CH═CH(CH$_2$)$_2$—; n is 0, 1 or 2; and R$^2$ is halogen, cyano, C$_1$ to C$_{12}$ alkyl, C$_2$ to C$_{12}$ alkenyl, or —y$^1$—X—y$^2$ wherein X is COO, OOC, CO, O, or a covalent bond, y1 is either not present or present as C$_1$ to C$_{12}$ alkyl or C$_2$ to C$_{12}$ alkenyl, where the alkyl or alkenyl is unsubstituted or substituted with at least one fluorine, and y$^2$ is C$_1$ to C$_{12}$ alkyl or C$_2$ to C$_{12}$ alkenyl, where the alkyl or alkenyl is unsubstituted or substituted with at least one fluorine.

25. An electro-optical cell comprising:

(a) two plate means;

(b) liquid crystal means disposed between the two plate means and including a compound having the formula:

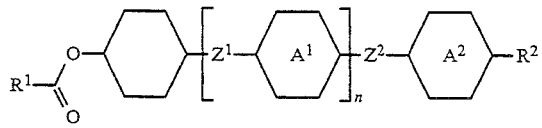

wherein

R$^1$ is a C$_2$ to C$_{12}$ alkenyl;

A$^1$ and A$^2$ each independently is an unsubstituted 1,4-phenylene, halogen substituted 1,4-phenylene, unsubstituted 1,4-phenylene in which one of the CH groups is replaced by nitrogen, unsubstituted 1,4-phenylene in which two of the CH groups are replaced by nitrogen, trans-1,4-cyclohexylene, or trans-1,3-dioxane-2,5-diyl;

Z$^1$ and Z$^2$ each independently is a single covalent bond, —CH$_2$CH$_2$—, —COO—, —OOC—, —OCH$_2$—, —CH$_2$O—, —C≡C—, —(CH$_2$)$_4$—, —O(CH$_2$)$_3$—, —(CH$_2$)$_3$O—, or the trans form of —OCH$_2$CH═CH—, —CH═CHCH$_2$O—, —(CH$_2$)$_2$CH═CH— or —CH═CH(CH$_2$)$_2$—; n is 0, 1 or 2; and R$^2$ is halogen, cyano, C$_1$ to C$_{12}$ alkyl, C$_2$ to C$_{12}$ alkenyl, or —y$^1$—X—y$^2$ wherein X is COO, OOC, CO, O, or a covalent bond, y$^1$ is either not present or present as C$_1$ to C$_{12}$ alkyl or C$_2$ to C$_{12}$ alkenyl, where the alkyl or alkenyl is unsubstituted or substituted with at least one fluorine, and y$^2$ is C$_1$ to C$_{12}$alkyl or C$_2$ to C$_{12}$ alkenyl; where the alkyl or alkenyl is unsubstituted or substituted with at least one fluorine; and (c) means for apply electric potential to the plate means.

* * * * *

UNITED STATES PATENT AND TRADEMARK OFFICE
CERTIFICATE OF CORRECTION

PATENT NO. : 5,380,462
DATED : January 10, 1995
INVENTOR(S) : Stephen Kelly and Martin Schadt It is certified that error appears in the above-identified patent and that said Letters Patent is hereby corrected as shown below:

Claim 1, column 21, line 67, delete "-C=C-" and insert therefor — $-C\equiv C-$ —;

Claim 1, column 22, line 7, delete "-y$^1$-X-y$^2$-" and insert therefor — $-Y^1-X-Y^2-$ —;

Claim 1, column 22, line 10, delete "y$^1$" and insert therefor — $Y^1$ —;

Claim 1, column 22, line 14, delete "y$^2$" and insert therefor — $Y^2$ —;

Claim 1, column 22, line 14, between "alkyl" and "C$_2$", add — or —;

Claim 3, column 22, line 18, delete "1 E-propenyl" and insert therefor — 1E-propenyl —;

Claim 6, column 22, line 61, delete "5 -diyl" and insert therefor — 5-diyl —;

Claim 6, column 22, line 64, delete "-COO-or" and insert therefor — -COO- or —;

Claim 7, column 23, line 16, delete "bona" and insert therefor — bond —;

Claim 11, column 23, line 66, delete "R1" and insert therefor — $R^1$ —;

Claim 11, column 23, line 66, delete "R2" and insert therefor — $R^2$ —;

Claim 13, column 24, line 21, delete "R1" and insert therefor — $R^1$ —;

Claim 24, column 25, line 47, between "crystalline" and "composition", delete — ; —;

Claim 24, column 26, line 5, delete "-C=C-" and insert therefor — $-C\equiv C-$ —;

Claim 24, column 26, line 6, delete "-(CH$_2$)$_3$C-" and insert therefor — -(CH$_2$)$_3$O- —;

Claim 24, column 26, line 12, delete "-y$^1$-X-y$^2$-" and insert therefor — $-Y^1-X-Y^2-$ —;

Claim 24, column 26, line 15, delete "y$^1$" and insert therefor — $Y^1$ —;

UNITED STATES PATENT AND TRADEMARK OFFICE
CERTIFICATE OF CORRECTION

PATENT NO. : 5,380,462

DATED : January 10, 1995

INVENTOR(S) : Stephen Kelly and Martin Schadt

It is certified that error appears in the above-identified patent and that said Letters Patent is hereby corrected as shown below:

Claim 24, column 26, line 19, delete "$y^2$" and insert therefor — $Y^2$ —;

Claim 25, column 26, line 46, delete "-C=C-" and insert therefor — $-C\equiv C-$ —;

Claim 25, column 26, line 52, delete "$y^1-X-y^2$" and insert therefor — $Y^1-X-Y^2$ —;

Claim 25, column 26, line 55, delete "$y^1$" and insert therefor — $Y^1$ —;

Claim 25, column 26, line 59, delete "$y^2$" and insert therefor — $Y^2$ —;

Signed and Sealed this

Twenty-first Day of March, 1995

Attest:

BRUCE LEHMAN

*Attesting Officer*     *Commissioner of Patents and Trademarks*